(12) United States Patent
Ko et al.

(10) Patent No.: US 11,457,973 B2
(45) Date of Patent: Oct. 4, 2022

(54) ENDOSCOPIC FULL THICKNESS RESECTION DEVICE

(71) Applicant: Boston Scientific Scimed, Inc., Maple Grove, MN (US)

(72) Inventors: Michael Y. Ko, Waltham, MA (US); John A. Hingston, Framingham, MA (US); Andrew Horowitz, Mansfield, MA (US); Kevin Windheuser, Hopkinton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 614 days.

(21) Appl. No.: 16/408,926

(22) Filed: May 10, 2019

(65) Prior Publication Data
US 2019/0343576 A1    Nov. 14, 2019

Related U.S. Application Data

(60) Provisional application No. 62/670,010, filed on May 11, 2018.

(51) Int. Cl.
*A61B 18/00* (2006.01)
*A61B 18/14* (2006.01)

(52) U.S. Cl.
CPC .. *A61B 18/149* (2013.01); *A61B 2018/00214* (2013.01); *A61B 2018/00494* (2013.01);
(Continued)

(58) Field of Classification Search
CPC .......... A61B 17/320016; A61B 18/149; A61B 2018/1475; A61B 2018/00214;
(Continued)

(56) References Cited

U.S. PATENT DOCUMENTS 6,125,852 A * 10/2000 Stevens ..................... A61F 7/10
                                                           128/898
7,651,491 B2    1/2010 Nobis et al.
(Continued)

OTHER PUBLICATIONS

International Search Report and Written Opinion for International Application No. PCT/US2019/031718, dated Aug. 5, 2019, 9 pages.
(Continued)

*Primary Examiner* — Linda C Dvorak
*Assistant Examiner* — Nicholas S Borsch
(74) *Attorney, Agent, or Firm* — Seager, Tufte & Wickhem, LLP

(57) ABSTRACT

The present disclosure relates generally to devices and methods for full thickness tissue resection of an organ (e.g., intestine). In some embodiments, a device includes a conduit, and a plurality of arms rotatably coupled to the conduit. Each of the plurality of arms is movable between a collapsed position and an expanded position, wherein the plurality of arms extends radially outward from the conduit in the expanded position. The device may further include an electrocautery wire coupled to each of the plurality of arms, the electrocautery wire positioned directly adjacent an exterior tissue wall when the plurality of arms is in the expanded position. The device may be advanced back in towards a lumen of the organ until a targeted section of tissue is cut by the electrocautery wire and removed.

17 Claims, 9 Drawing Sheets

(52) U.S. Cl.
CPC .............. *A61B 2018/00595* (2013.01); *A61B 2018/00601* (2013.01); *A61B 2018/1475* (2013.01)

(58) Field of Classification Search
CPC .. A61B 2018/0016; A61B 2018/00595; A61B 2018/00601; A61B 2018/00607
USPC .............................................. 606/45, 46, 47
See application file for complete search history.

(56) References Cited

U.S. PATENT DOCUMENTS

| | | | |
|---|---|---|---|
| 8,414,596 B2* | 4/2013 | Parihar | A61B 17/00234 606/127 |
| 2004/0034380 A1* | 2/2004 | Woolfson | A61F 2/2427 606/170 |
| 2006/0064113 A1* | 3/2006 | Nakao | A61B 17/320016 606/113 |
| 2008/0125797 A1* | 5/2008 | Kelleher | A61B 17/1114 606/153 |
| 2014/0046320 A1 | 2/2014 | Kappel et al. | |
| 2017/0333114 A1* | 11/2017 | Atwell | A61B 18/1445 |

OTHER PUBLICATIONS

Jablons, J., "Utilizing Tungsten Wire in Medical Device Applications", Datasheet [online] Metal Cutting Corporation, 2015 [retrieved on Oct. 25, 2019]. Retrieved from Internet URL: https://metalcutting.com/utilizing-tungsten-wire-in-medical-device-applications/, 5 pages.

Author unknown, "Innovation in Scope", Datasheet [online] Ovesco, 2019 [retrieved on Oct. 15, 2019]. Retrieved from Internet URL: http://www.ovesco.com/index.phpid=32, 2 pages.

* cited by examiner

ENDOSCOPIC FULL THICKNESS RESECTION DEVICE

CROSS REFERENCE TO RELATED APPLICATIONS

This application claims the benefit of priority under 35 U.S.C. § 119 to U.S. Provisional Patent Application Ser. No. 62/670,010, filed on May 11, 2018, which is incorporated by reference in its entirety for all purposes.

FIELD

The present disclosure relates generally to resection devices and, more particularly, to endoscopic full thickness resection devices for resection of tissue in the lower gastrointestinal tract.

BACKGROUND

Resectioning procedures involve excising a portion of an organ, reconnecting the surrounding sections together to close up the hole created by the excision, and removing the excess tissue resulting from the procedure. Some devices are available for resectioning lesions in tubular organs. Several known resectioning devices require at least one incision in an area near the portion of the organ to be excised because, for example, the resectioning device may lack steering and/or viewing capabilities.

With deep invasive cancers, such as T1 and T2 lesions, it is difficult to perform resection using conventional minimally invasive endoscopic procedures, such as endoscopic mucosal resection (EMR) and Endoscopic Submucosal Dissection (ESD), because these procedure are only able to remove cancerous tissue no deeper than the submucosal layer. Intentional full thickness resection (FTR) is an alternative approach, but has a high risk profile. Challenges for FTR include post-operative leakage, and awareness of adjacent anatomy. With current techniques and devices, the endoscopic treatment of non-lifting lesions or deep submucosal or muscular invasion is difficult. When FTR is not an option to safely remove deeper-reaching cancers, laparoscopic surgery, which is more invasive and increases patient risk, is often the next approach.

SUMMARY

The present disclosure in its various embodiments relates generally to devices and methods for performing endoscopic full thickness resection of tissue in the lower gastrointestinal tract. In one or more embodiments, a tissue resection device may include a conduit, and a plurality of arms rotatably coupled to the conduit. In one or more embodiments, the plurality of arms is movable between a collapsed position and an expanded position, wherein the plurality of arms extends radially outward from the conduit in the expanded position. The tissue resection device may further include an electrocautery wire coupled to the plurality of arms, the electrocautery wire positionable directly adjacent an exterior tissue wall when the plurality of arms is in the expanded position. In one or more embodiments, the tissue resection device may further include an electrocautery tip extending from the plurality of arms, the electrocautery tip operable to perforate an interior tissue wall. In one or more embodiments, the electrocautery tip may be integrally coupled with one or more of the plurality of arms. In one or more embodiments, the tissue resection device may include a control wire coupled to the plurality of arms and to the conduit, wherein the control wire is operable to move the arms between the collapsed position and the expanded position. In one or more embodiments, the control wire may extend through an opening in the conduit. In one or more embodiments, the control wire may be directly coupled to each of the plurality of arms. In one or more embodiments, each of the plurality of arms may include a proximal end directly coupled to the conduit, and a distal end opposite the proximal end. The distal end may include an opening receiving the electrocautery wire. In one or more embodiments, the tissue resection device may include a tissue latching barb extending from the distal end of each of the plurality of arms, wherein the tissue latching barb extends substantially perpendicularly from the distal end of each of the plurality of arms when the plurality of arms is in the expanded position. In one or more embodiments, the plurality of arms may include three arms positioned circumferentially apart from one another by approximately 120°. In one or more embodiments, the plurality of arms may include two arms positioned circumferentially apart from one another by approximately 180°. In one or more embodiments, the electrocautery wire may be a single wire extending between each of the plurality of arms to form a substantially triangular outline. In one or more embodiments, the tissue resection device may include a cover extending between each of the plurality of arms, the cover operable to capture a targeted section of tissue.

In one or more embodiments, an endoscopic full thickness resection device may include a conduit, and a plurality of arms rotatably coupled to the conduit. Each of the plurality of arms may be movable between a collapsed position and an expanded position. Each of the plurality of arms may extend radially outward from the conduit in the expanded position. In one or more embodiments, the endoscopic full thickness resection device may include an electrocautery wire extending between a distal end of each of the plurality of arms, the electrocautery wire positioned directly adjacent an exterior tissue wall when the plurality of arms is in the expanded position. In one or more embodiments, the endoscopic full thickness resection device may include an electrocautery tip extending from the plurality of arms. The electrocautery tip may be operable to perforate an interior tissue wall when the plurality of arms is in the collapsed position. In one or more embodiments, the endoscopic full thickness resection device may include a control wire coupled between the plurality of arms and the conduit, wherein the control wire is operable to move the arms between the collapsed position and the expanded position.

In one or more embodiments, a method for tissue resection may include positioning a tissue resection device within a lumen of an organ. The tissue resection device may include a conduit, and a plurality of arms rotatably coupled to the conduit, wherein each of the plurality of arms is movable between a collapsed position and an expanded position. The tissue resection device may further include an electrocautery wire coupled to the plurality of arms. The method may further include penetrating a wall of the organ with the tissue resection device, and extending the plurality of arms radially outward from the conduit to the expanded position. The electrocautery wire may be positioned directly adjacent an exterior of the wall of the organ. The method may further include retracting the tissue resection device towards the lumen of the organ to resection a targeted section of the wall. In one or more embodiments, the method may further include energizing the electrocautery wire after the electrocautery wire is brought into position directly adjacent the exterior of the wall of the organ, and contacting the exterior of the wall of the organ with the electrocautery wire to penetrate the wall of the organ. In one or more embodiments, the method may further include providing an electrocautery tip extending from the plurality of arms, and perforating, when the plurality of arms is in the collapsed position, an interior tissue wall of the organ using the electrocautery tip. In one or more embodiments, the method may further include biasing the plurality of arms between the collapsed and expanded positions using a control wire coupled between the plurality of arms and the conduit. In one or more embodiments, the method may further include engaging the wall of the organ with a set of tissue latching barbs. In one or more embodiments, the method may further include retracting the tissue resection device into an endoscopic tissue clamping device, and securing a fastener around an opening in the wall of the organ, wherein the opening is formed by removal of the targeted section of the wall.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Embodiments herein disclose tissue resection devices and methods for minimally invasive FTR. Those skilled in the art will appreciate that while the devices and approaches of the present disclosure will herein be described with reference to FTR of the colon, the devices and approaches may be utilized in other digestive tract transluminal procedures, and may be introduced transorally as well as transanally.

In some approaches, a resection device may perform FTR by accessing the outside of an organ (e.g., large intestine) wall from inside of a lumen, and then advancing back in towards the lumen until the targeted section of tissue is removed. Cutting may be performed by means of electrocautery, a process by which soft tissue is destroyed or cut using heat conduction from a metal probe heated by electric current. The electrocautery approach allows for hemostasis during the procedure, and minimizes opportunity for postoperative leakage. In some approaches, the resection device includes an electrocauterizing tip used to gain access to the outside of the colon wall with precision and minimal opportunity to damage adjacent anatomy.

Various embodiments herein may include a plurality of arms rotatably coupled to a conduit, each of the plurality of arms movable between a collapsed position and an expanded position. The plurality of arms may extend radially outward from the conduit in the expanded position until each of the plurality of arms are perpendicular, or substantially perpendicular, to an exterior surface of the conduit. In some embodiments, a control wire may be coupled between the plurality of arms and the conduit. The control wire is operable to move the arms between the collapsed position and the expanded position. In non-limiting embodiments, the control wire may extend through an opening in the conduit.

An electrocautery wire may be coupled to each of the plurality of arms and positioned directly adjacent an exterior tissue wall when the plurality of arms is in the expanded position. During use, the electrocautery wire is energized and then brought into contact with the exterior tissue wall to cut the tissue from the outside. Various embodiments herein may include the electrocautery tip extending from the plurality of arms to initially perforate an interior tissue wall when the plurality of arms is in the collapsed position. The electrocautery tip may be integrally coupled with one or more of the plurality of arms, or may be a separate cauterizing tool that extends from the conduit.

Figure 1:
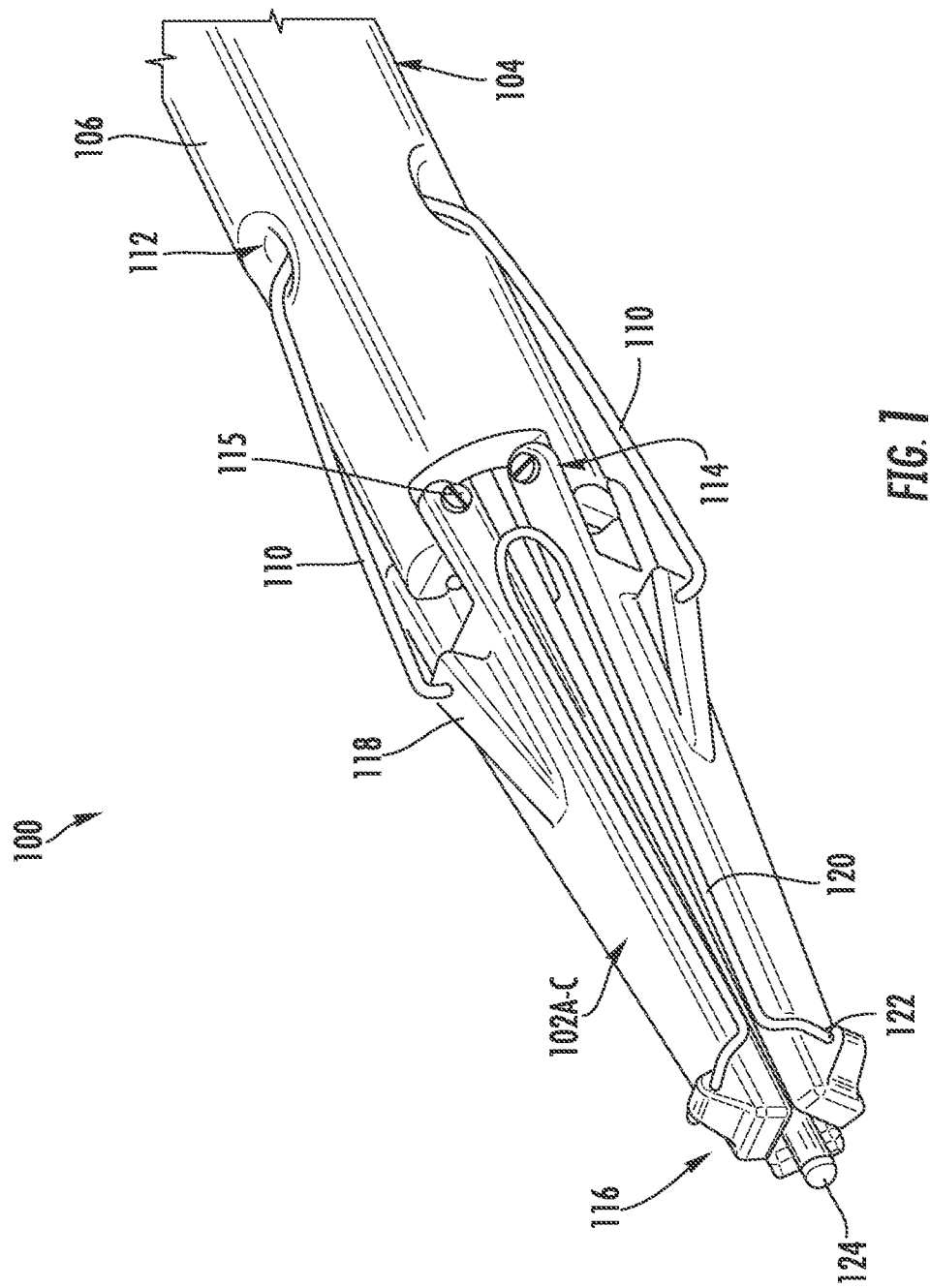
FIG. 1 is a perspective view of a resection device in a collapsed position according to embodiments of the present disclosure.
Figure 2:
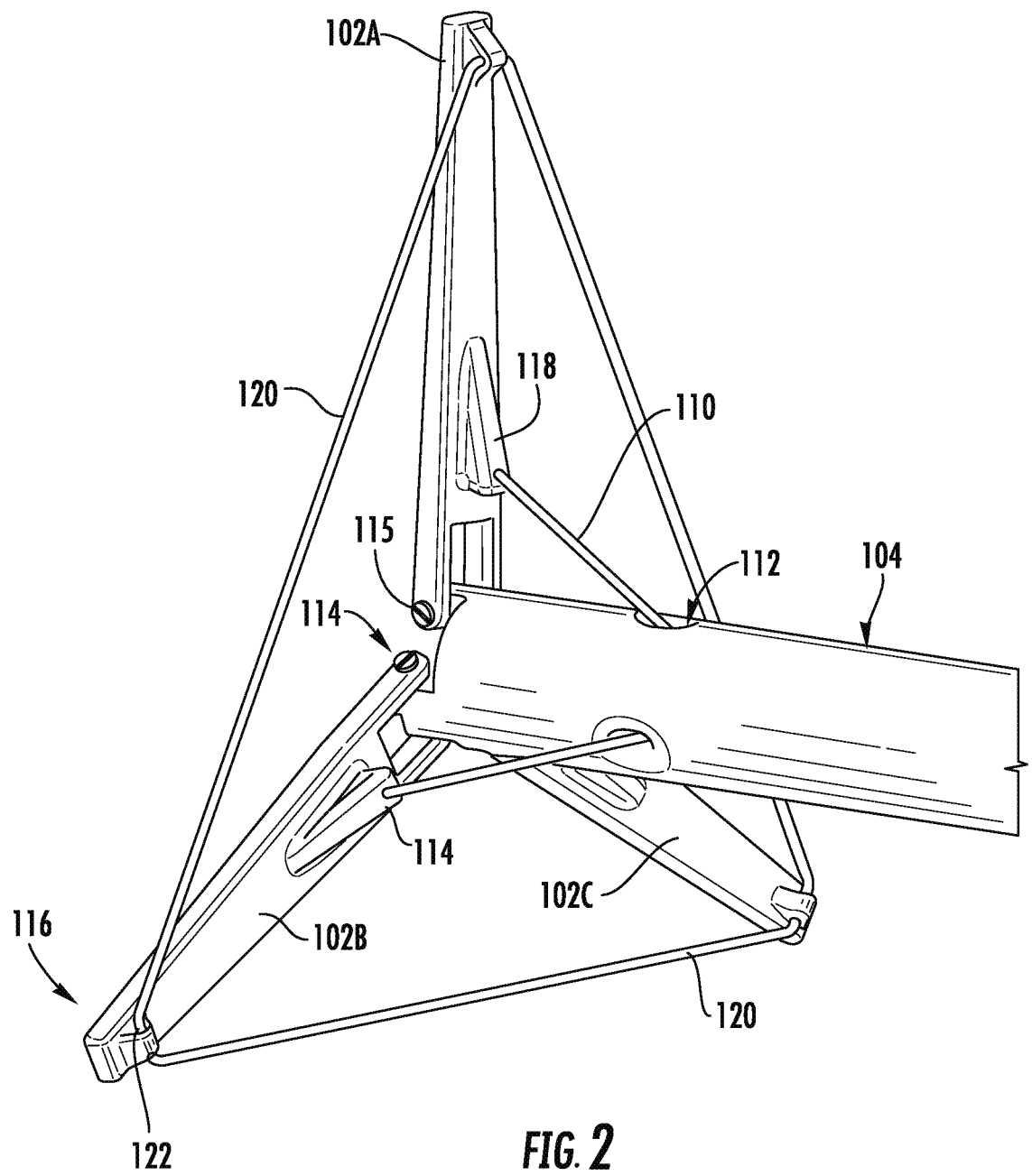
FIG. 2 is another perspective view of the resection device of FIG. 1 in an expanded position according to embodiments of the present disclosure.

Turning now to FIGS. 1-2, a FTR device (hereinafter "device") 100 according to embodiments of the disclosure will be described in greater detail. As shown, the device 100 may include a plurality of arms 102A-C rotatably coupled to a conduit 104, which may be a hollow tube for insertion within a bodily lumen. The plurality of arms 102 may initially be in a collapsed position, demonstrated in FIG. 1, in which the plurality of arms 102 are in abutment with one another. In some embodiments, the plurality of arms 102 extend in an axial direction from an end of the conduit 104 when in the collapsed position. In the expanded configuration, demonstrated in FIG. 2, the plurality of arms 102A-C may extend radially outward from the conduit 104 until each of the plurality of arms 102A-C is perpendicular, or substantially perpendicular, to an exterior surface 106 of the conduit 104. In some embodiments, the plurality of arms 102A-C are arranged evenly about a central axis extending through the conduit 104. For example, each of the plurality of arms 102A-C may be spaced apart from one another by approximately 120° around the circumference of the conduit 104. In other embodiments, a greater or fewer number of arms may be present.

The plurality of arms 102A-C each include a proximal end 114 rotatably coupled to the conduit, e.g., by a hinge 115, and a distal end 116 opposite the proximal end 114. During operation, a user can interface with a handle (not shown) coupled with a slider that may be pulled or pushed to manipulate the plurality of arms 102A-C between the collapsed and expanded positions. In some embodiments, the handle may have a detent, or other tactical feature, and a visual indicator that can provide information to the user regarding the position of the plurality of arms 102A-C.

As further shown, the device 100 may include one or more control wires 110 coupled between the plurality of arms 102A-C and the conduit 104. The control wires 110 are operable to move the plurality of arms 102A-C between the collapsed position and the expanded position. The control wires 110 may extend through an interior of the conduit 104, and exit through one or more openings 112 for connection with the plurality of arms 102A-C. In some embodiments, the control wires 110 are directly/mechanically coupled to each of the plurality of arms 102A-C. For example, the plurality of arms 102A-C may include any variety of mechanical fasteners or retainers 118 operable to fix an end of each of the control wires 110 therein.

The device 100 may further include an electrocautery wire 120 coupled to each of the plurality of arms 102A-C, for example, at the distal ends 116 thereof. The electrocautery wire 120 may extend through an opening 122 at the distal end 116 of each of the plurality of arms 102A-C. The electrocautery wire 120 may be folded along the plurality of arms 102A-C when in a collapsed position, and extend tautly between the distal ends 116 of the plurality of arms 102A-C when in an expanded position. In some embodiments, the electrocautery wire 120 is a single contiguous wire extending between each of the plurality of arms 102A-C. In the expanded position of the plurality of arms 102A-C, the electrocautery wire 120 may take on a substantially triangular shape/outline. One or skill in the art will appreciate that a different number of arms may alter the shape of the expanded electrocautery wire 120 and, therefore, the area of the tissue being resected. For example, four arms may result in a square-shaped expanded electrocautery wire 120, five arms may result in a hexagonal-shaped expanded electrocautery wire 120, and so on. As will be described in greater detail below, the electrocautery wire 120 may be positioned directly adjacent an exterior tissue wall when the plurality of arms 102A-C is in the expanded position to enable tissue resection.

In one embodiment, the electrocautery wire 120 is a tungsten wire capable of burning/cutting tissue to remove and/or close off a part of the tissue, in a process called cautery. For example, the electrocautery wire 120 is supplied an electric current, and then applied to the targeted tissue for resection thereof. Tungsten has the ability to hold its shape and not flex or deform at the temperatures resection procedures typically require in order to efficiently cut and cauterize tissue. In exemplary embodiments, the plurality of arms 102A-C are electrically non-conductive.

As further shown, the device 100 may include an electrocautery tip 124 extending from the plurality of arms 102A-C to initially perforate an interior tissue wall when the plurality of arms is in the collapsed position. The electrocautery tip 124 may be integrally coupled with one or more of the plurality of arms 102A-C, or may be a separate cauterizing tool that extends from an interior of the conduit 104. The electrocautery tip 124 may be electrically conductive, and receive an electrical current to raise the temperature of the electrocautery tip 124. During use, the electrocautery tip 124 may burn/cut a small hole into the tissue (e.g., the colon wall) to gain access therethrough. In an exemplary embodiment, the electrocautery tip 124 and the electrocautery wire 120 may receive current independently. In other embodiments, the electrocautery tip 124 may be replaced or supplemented with one or more cutting instruments capable of perforating the tissue wall.

In operation, a distal end of the device 100 may be inserted from a proximal end of an endoscope through the biopsy/working channel port. The device 100 may be operated while the distal end is within the field of view of the scope's camera lens. As such, an operator is able to see the operating end of the device 100 and tissue target, while cauterizing from the lumen to the outside of the colon, thus giving the operator visible indication of depth of cut and awareness of adjacent anatomy.

Turning now to FIGS. 3A-3E, a non-limiting approach for endoscopic FTR, for example of the colon, will be described in greater detail. As shown, the device 100 includes many or all of the features previously described in relation to the device 100 of FIGS. 1-2. However, just certain aspects of the device 100 will hereinafter be described for the sake of brevity.

Figure 3A:
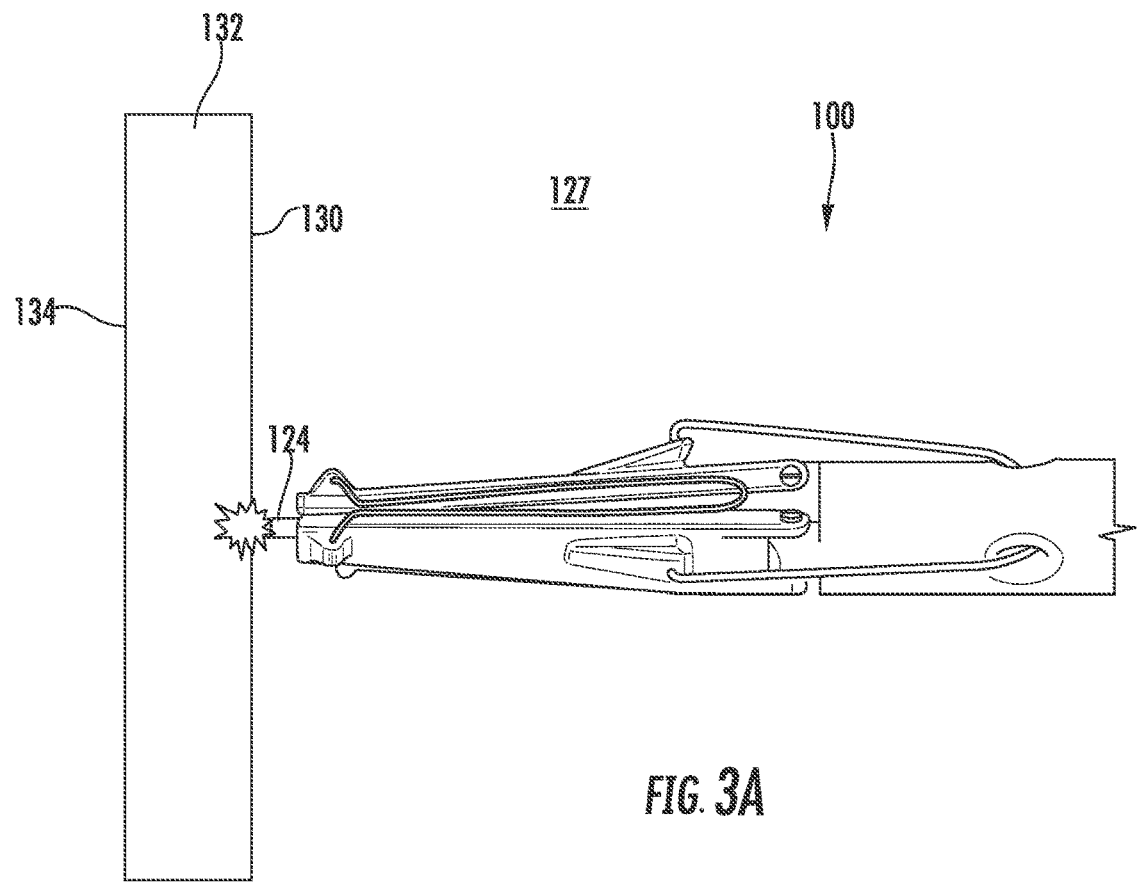
FIGS. 3A-3E are side views of the resection device of FIG. 1 in operation with an organ according to embodiments of the present disclosure.
Figure 3B:
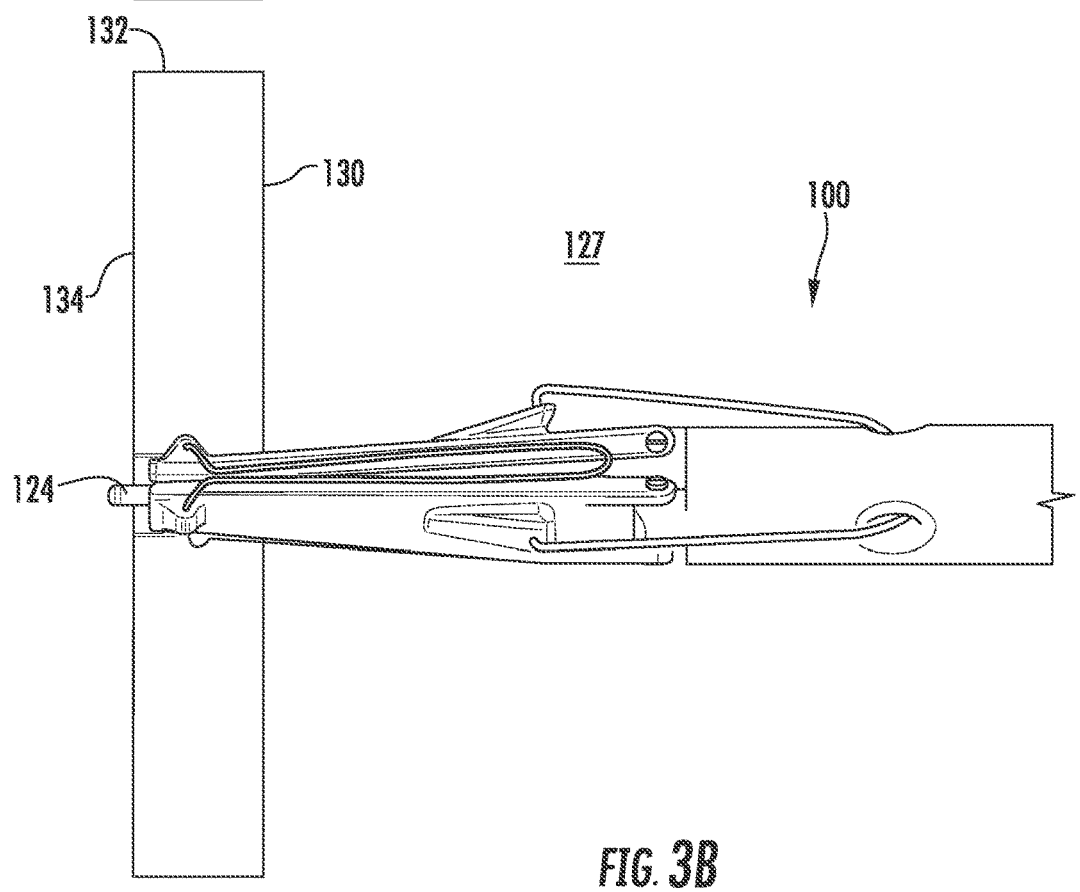

As shown in FIG. 3A, the device 100 is positioned inside a lumen 127 of the colon 132 and brought into position proximate an interior wall (i.e., mucosa) 130 of the colon 132. The electrocautery tip 124 may then be activated to raise the temperature thereof. The electrocautery tip 124 then penetrates the interior wall 130, as shown in FIG. 3A, and continues through the colon 132 until an outer wall (i.e., serosa) 134 is also breached, as shown in FIG. 3B. If a separate tool, the electrocautery tip 124 can be removed after perforation is made fully through the colon 132.

Figure 3C:
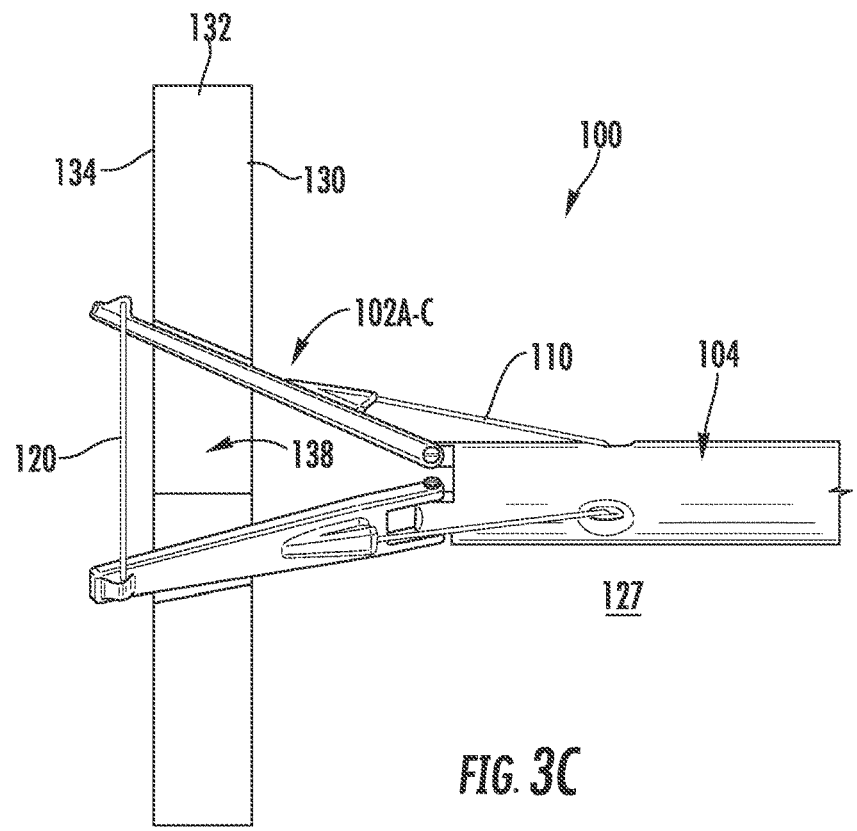

Next, as shown in FIG. 3C, the plurality of arms 102A-C may begin expanding radially away from one another and from the conduit 104 as the device 100 continues towards the outer wall 134 of the colon 132. In some embodiments, the control wires 110 may be drawn into the conduit 104, causing the plurality of arms 102A-C to fold back towards the conduit 104. As shown, the plurality of arms 102A-C may press against the colon 132, causing an opening 138 formed therein to be enlarged.

Figure 3D:
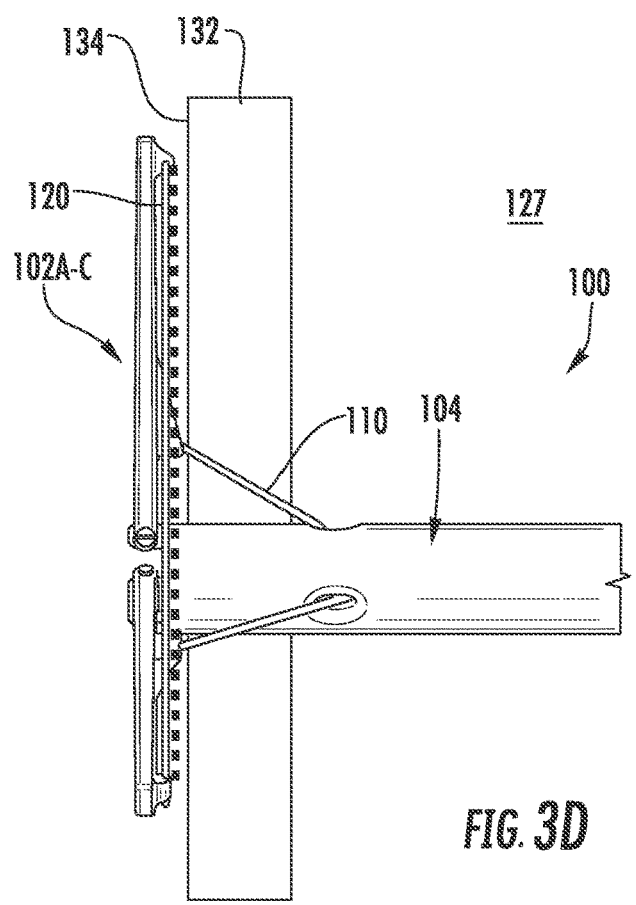
Figure 3E:
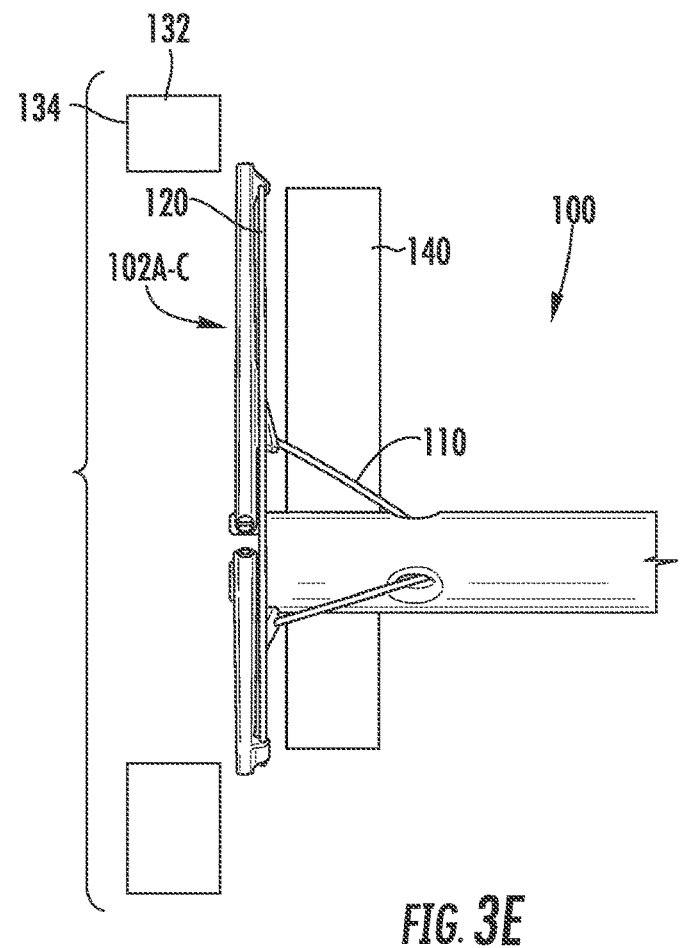

As shown in FIG. 3D, the conduit 104 may be inserted though the opening 138, as the plurality of arms 102A-C are drawn to a perpendicular, or substantially perpendicular, position relative to the conduit 104. Once the plurality of arms 102A-C are fully expanded, the plurality of arms 102A-C may be positioned directly adjacent the outer wall 134 of the colon 132, and the electrocautery wire 120 is taut. The device 100 may be pulled back towards the colon 132 into position directly adjacent the outer wall 134 of the colon 132. The electrocautery wire 120 may then be energized, and the device 100 advanced back towards the lumen 127 until a targeted section 140 of the colon 132 is resected, as shown in FIG. 3E. The targeted section 140 may then be brought into an interior of the lumen for subsequent removal.

Figure 4:
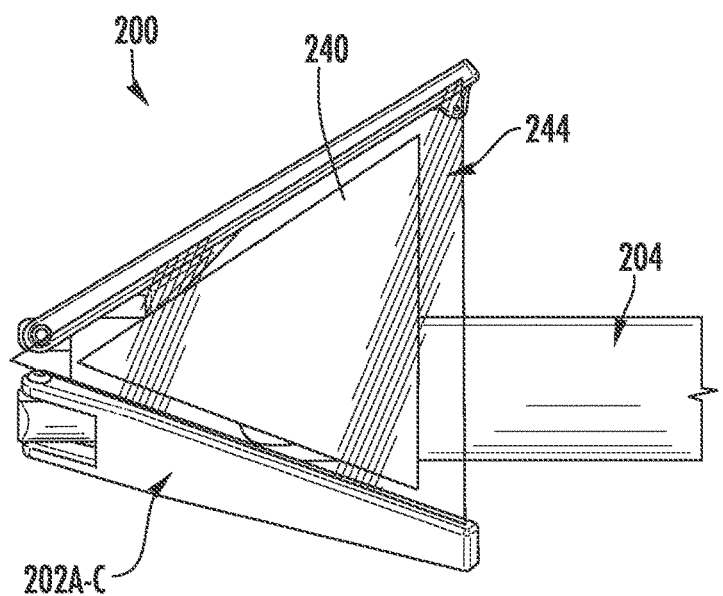
FIG. 4 is a side view of a resection device including a covering according to embodiments of the present disclosure.

In another embodiment of the present disclosure, as shown in FIG. 4, a FTR device 200 may include a shroud or covering 244 extending between the plurality of arms 202A-C to collect the resected targeted section 240. As shown, the device 200 includes many or all of the features previously described in relation to the device 100 of FIGS. 1-3E. However, just certain aspects of the device 200 will hereinafter be described for the sake of brevity.

In various embodiments, the covering 244 may include three or more separate components coupled between adjacent arms of the plurality of arms 202A-C, or may be a single contiguous component. Although not limited to any particular material, the covering 244 may be a transparent or translucent flexible polymer. In some embodiments, to aid with retention of the resected targeted section 240, the plurality of arms 202A-C may invert and fold back towards the conduit 204.

Figure 5:
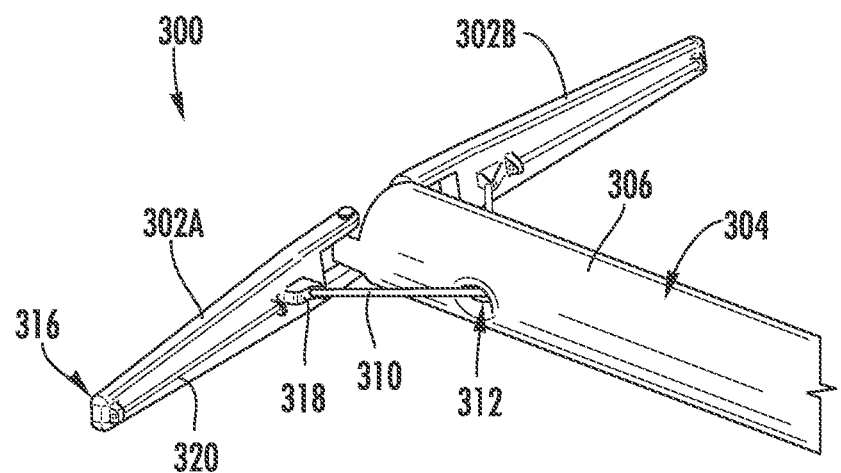
FIG. 5 is a perspective view of a resection device having a pair of arms according to embodiments of the present disclosure.

Turning now to FIG. 5, a FTR device (hereinafter "device") 300 according to embodiments of the disclosure will be described in greater detail. As shown, the device 300 may include a pair of arms 302A-B rotatably coupled to a conduit 304, which may be a hollow tube. Each of the pair of arms 302A-B is movable between a collapsed position (not shown) and the expanded position shown. In the expanded configuration, the pair of arms 302A-B may extend radially outward from the conduit 304 until each of the pair of arms 302A-B is perpendicular, or substantially perpendicular, to an exterior surface 306 of the conduit 304. As shown, each of the pair of arms 302A-B may extend along a same plane. In some embodiments, the pair of arms 302A-B are positioned apart from one another by approximately 180° around the circumference of the conduit 304.

As further shown, the device 300 may include one or more control wires 310 coupled between the pair of arms 302A-B and the conduit 304. The control wires 310 are operable to move the pair of arms 302A-B between the collapsed position and the expanded position. The control wires 310 may extend through an interior of the conduit 304, and exit through one or more openings 312 for connection with the pair of arms 302A-B. In some embodiments, the control wires 310 are directly/mechanically coupled to each of the pair of arms 302A-B using any variety of mechanical fasteners or retainers 318.

The device 300 may further include an electrocautery wire 320 coupled to each of the pair of arms 302A-B. The electrocautery wire 320 may extend between a distal end 316 and the mechanical retainers 318 of each of the pair of arms 302A-B. As shown, the electrocautery wire 320 may include two separate electrocautery wires. In other embodiments, the electrocautery wire 320 may be a contiguous wire extending between each of the pair of arms 302A-B. In the expanded position of the pair of arms 302A-B, the electrocautery wire 320 may extend along a same straight line.

Figure 6:
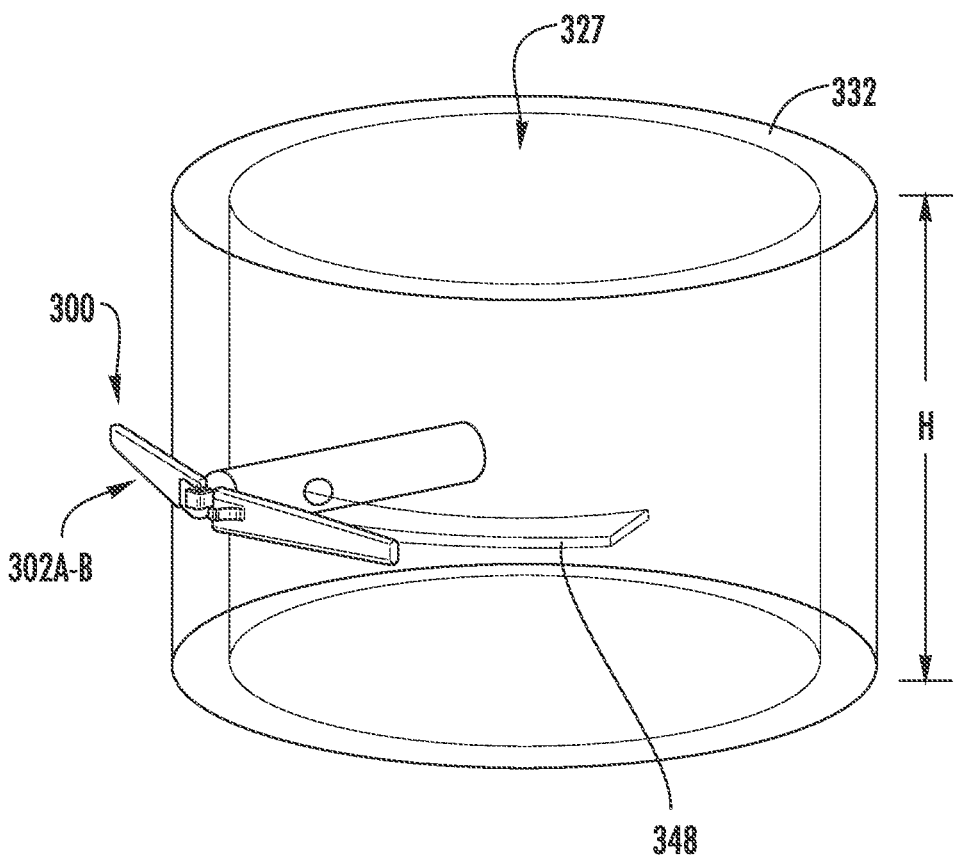
FIG. 6 is a side perspective view of the resection device of FIG. 5 in operation with an organ according to embodiments of the present disclosure.

During use, as shown in FIG. 6, the device 300 may be partially inserted though the colon 332, and the pair of arms 302A-B may be drawn to a perpendicular position relative to the conduit 304. Once the pair of arms 302A-B are fully expanded, and the electrocautery wire is energized, the device 300 may be rotated around a circumference of the colon 332 to form a slot 348 therein. Cutting may continue until the slot 348 extends 360° around the colon 332. The electrocautery wire may be de-energized, and the pair of arms 302A-B may then be collapsed and drawn into the lumen 327 of the colon 332. The device 300 may then be moved to a second axial position above or below the slot 348 along a height 'H' of the colon 332, and a second slot (not shown) may be formed 360° around the colon 332 to cut out a diseased tissue section.

Figure 7B:
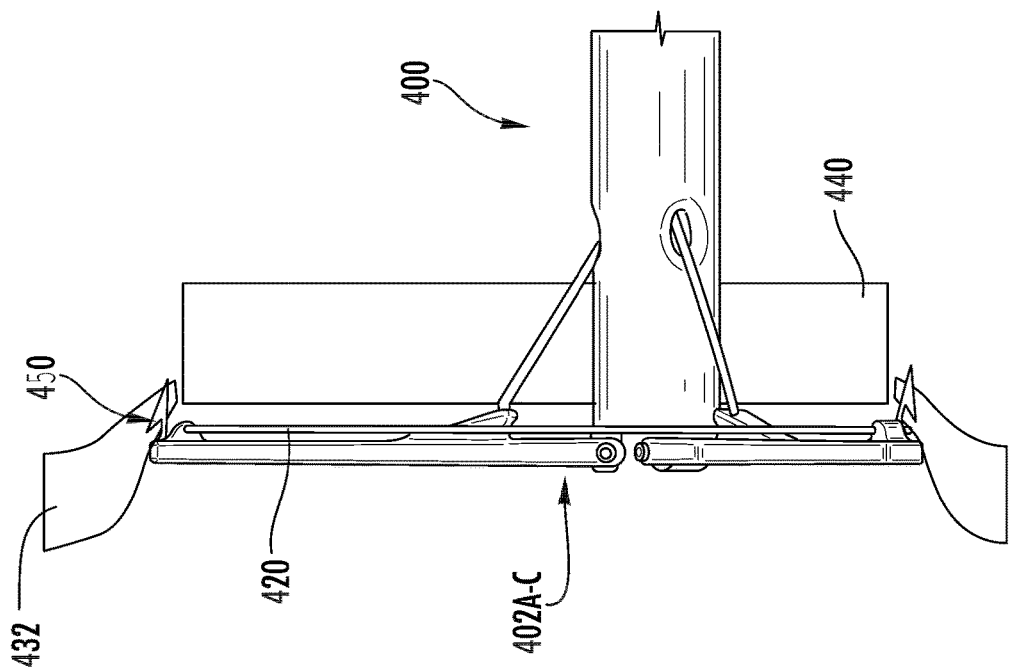
FIGS. 7A-7C are side views of a resection device including a set of tissue latching barbs in operation with an organ according to embodiments of the present disclosure.
Figure 7A:
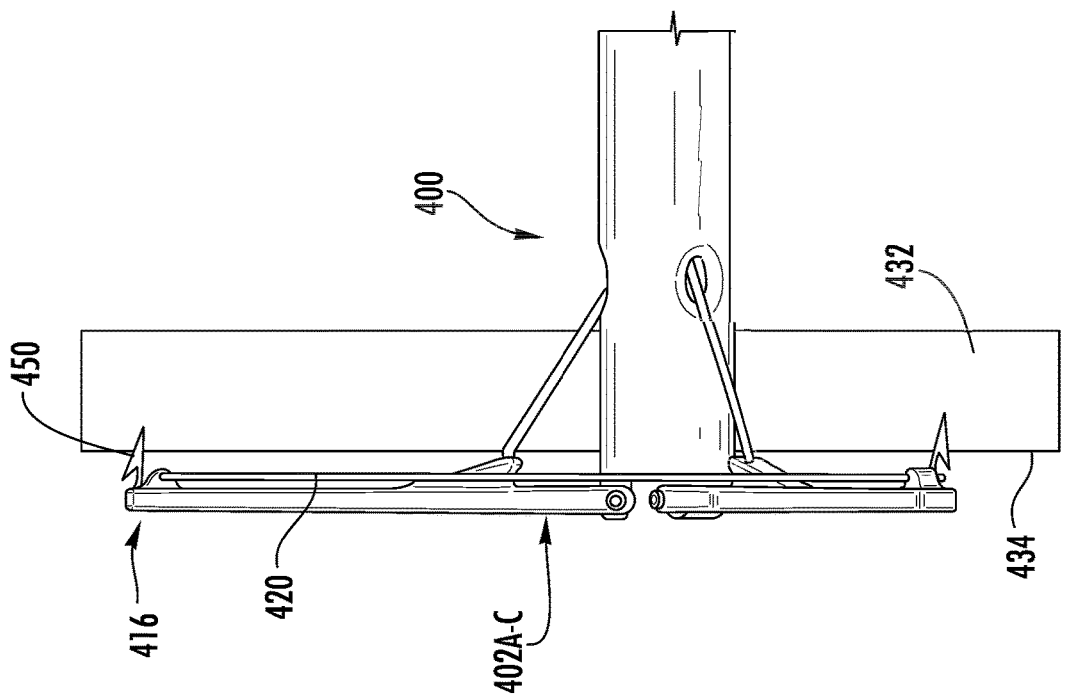
Figure 7C:
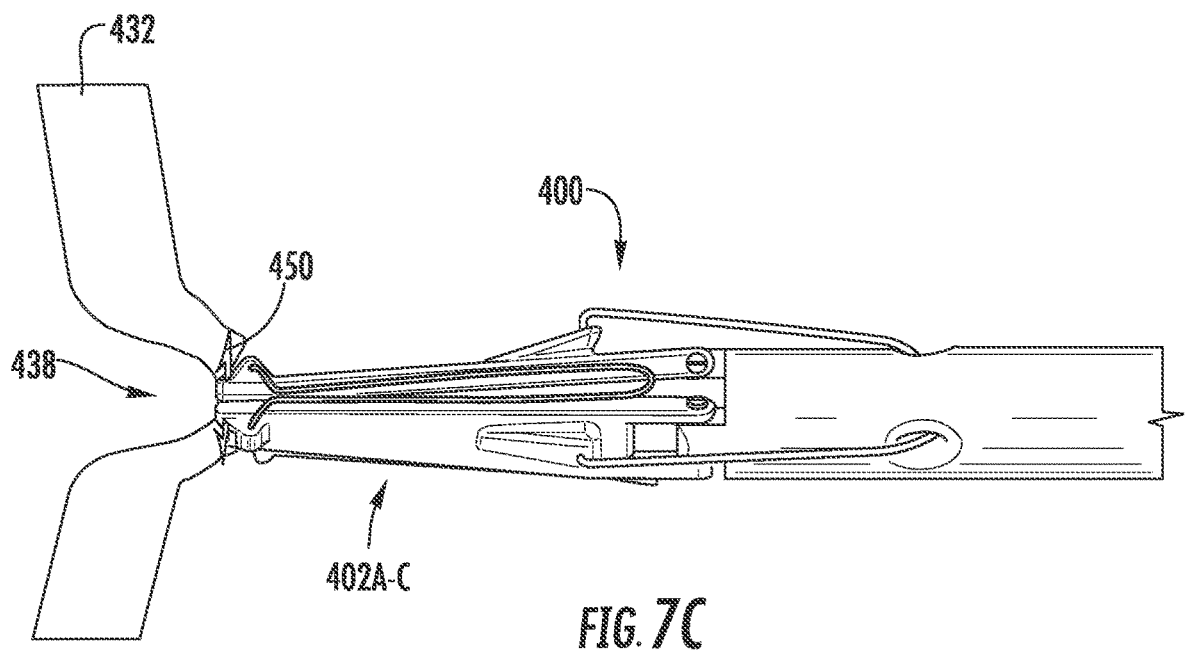

Turning now to FIGS. 7A-7C, a resection device (hereinafter "device") 400 according to some embodiments of the present disclosure will be described in greater detail. As shown, the device 400 may include one or more anchors, hooks, or tissue latching barbs 450 extending from the distal end 416 of each of the plurality of arms 402A-C. The tissue latching barbs 450 may extend perpendicularly, or substantially perpendicularly, from the distal end 416 of each of the plurality of arms 402A-C when the plurality of arms 402A-C is in the expanded position. In some embodiments, the tissue latching barbs 450 are collapsible along the plurality of arms 402A-C to permit the device 400 to more easily pass through the colon 432 with minimal interference and/or tissue damage. As demonstrated in FIG. 7A, the tissue latching barbs 450 engage the colon 432, and the electrocautery wire 420 is energized to begin cutting the outer wall 434. The surrounding tissue of the colon 432 may be hooked onto the plurality of arms 402A-C while resection of the targeted section 440 is performed, as demonstrated in FIG. 7B.

Figure 8:
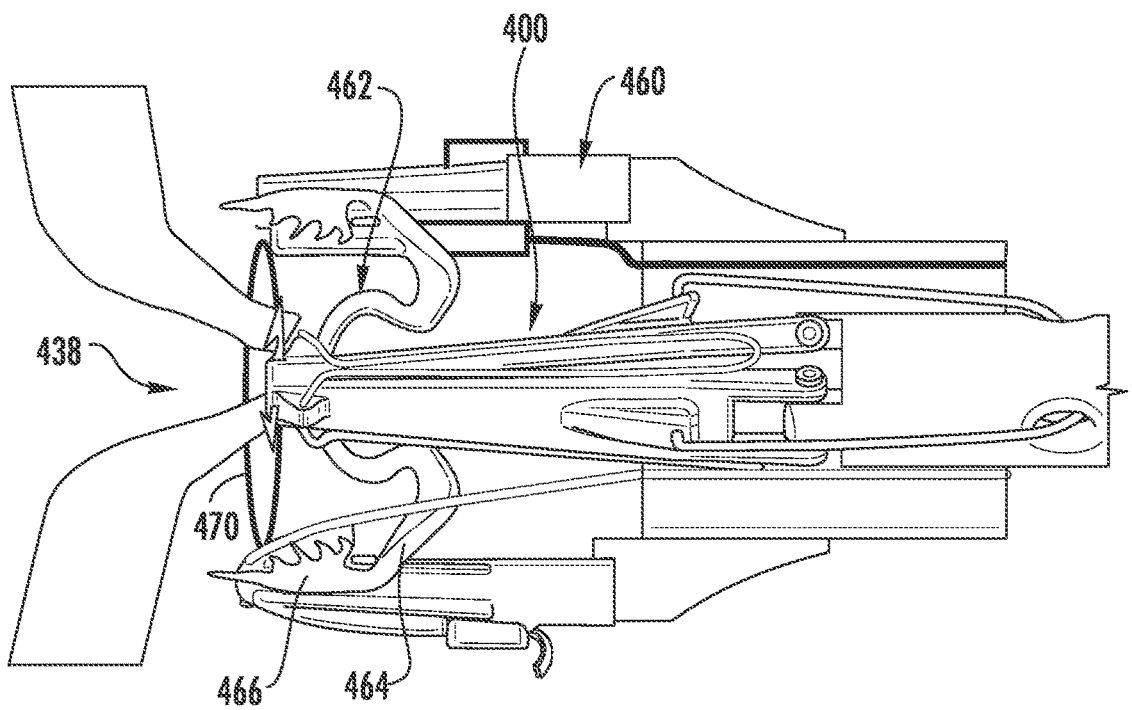
FIG. 8 is a side view of the resection device of FIGS. 7A-7C and an endoscopic tissue clamping device according to embodiments of the present disclosure.

The plurality of arms 402A-C may then be collapsed and brought together, as demonstrated in FIG. 7C. The tissue latching barbs 450 may continue to retain the tissue of the colon 432, thus shrinking the opening 438 formed by the resection as the plurality of arms 402A-C move towards one another. In non-limiting embodiments, as shown in FIG. 8, the device 400 may be retracted back into an endoscopic tissue clamping device 460, which releases a fastener, such as clip 462, to close the opening 438 in the colon 432. The endoscopic tissue clamping device 460 may include an electrocautery wire 470 to cut and cauterize a portion of the colon 432 proximal the clip 462 after the clip 462 is secured to the colon 432. The endoscopic tissue clamping device 460 and the device 400 may then be removed from the lumen of the colon 432.

In some embodiments, the clip 462 is provided to lessen the likelihood of internal leakage of body fluids. Although non-limiting, the clip 462 may be made of a shape-memory material, such as a nickel-titanium (Ni—Ti) alloy, and include two compression elements 464 and two, usually toothed, securing elements 466. The compression elements 464 and the securing elements 466 may be linear or curvilinear. Metals or alloys, such as stainless steel or other titanium alloys, and even certain plastic materials, may be used in fabricating the compression elements 464 and the securing elements 466.

When closed on the tissue of the colon 432, a constant compressive force acts between the two compression elements 464. In some embodiments, the constant force is independent of variation in tissue thickness being compressed. The ability to generate a constant force within a wide range of deformations ensures that the clip 462 is equally effective irrespective of the thickness of the compressed tissue. The clip 462, being sutureless, promotes hemostasis and a liquid tight seal, which is beneficial for aseptic healing.

Figure 9:
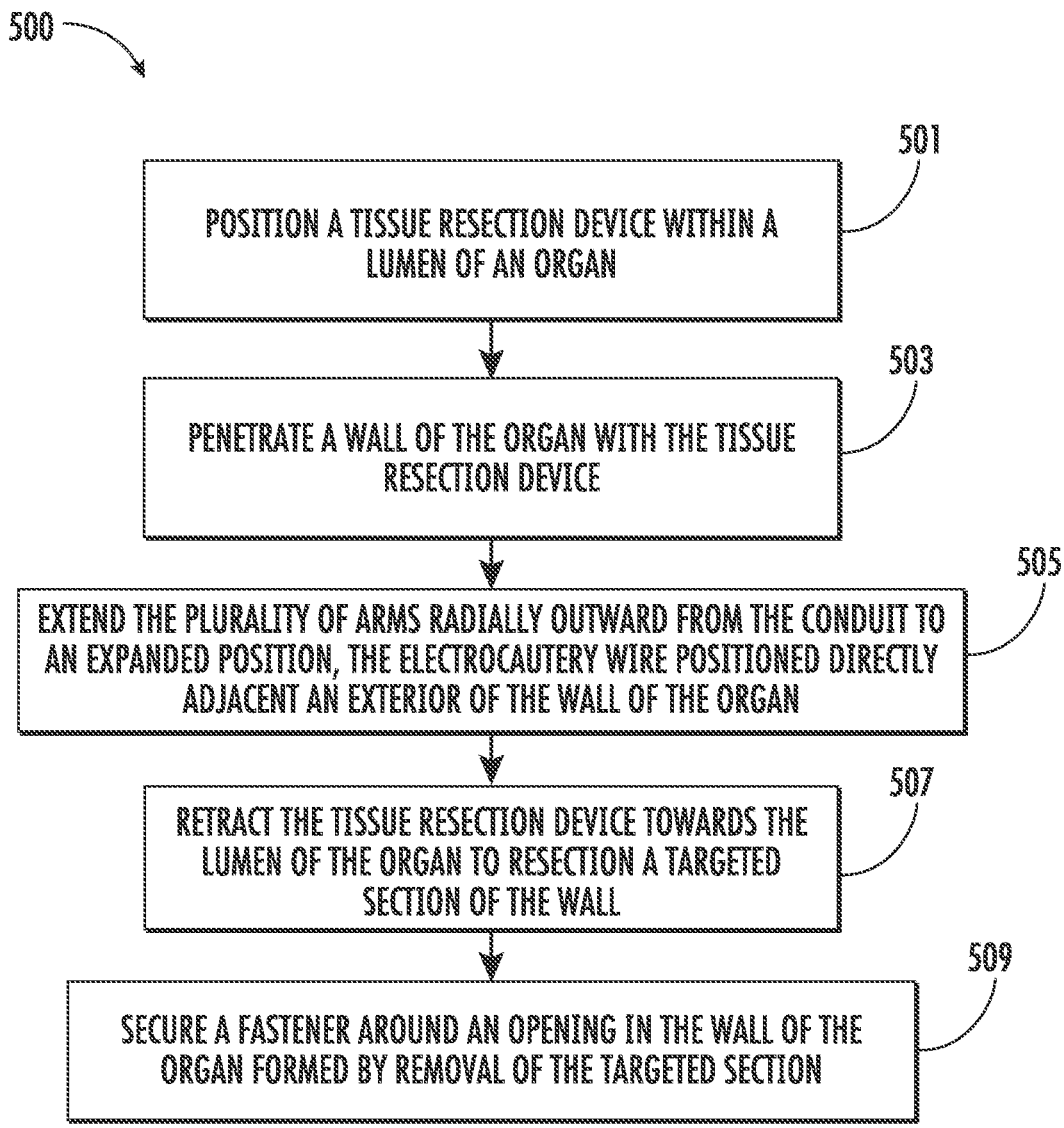
FIG. 9 is a flow diagram of a method for performing tissue resection according to embodiments of the present disclosure.

FIG. 9 is a flow diagram of a method 500 for performing tissue resection according to embodiments of the present disclosure. In block 501, the method 500 may include positioning a tissue resection device within a lumen of an organ, such as the intestine. In some embodiments, the tissue resection device includes a conduit, and a plurality of arms rotatably coupled to the conduit. Each of the plurality of arms is movable between a collapsed position and an expanded position. The tissue resection device may further include an electrocautery wire coupled to the plurality of arms.

At block 503, the method 500 may include penetrating a wall of the organ with the tissue resection device. In some embodiments, the wall is initially penetrated from within the lumen. In some embodiments, block 503 may include providing an electrocautery tip extending from the plurality of arms, and perforating, when the plurality of arms is in the collapsed position, an interior tissue wall using the electrocautery tip.

At block 505, the method 500 may include extending the plurality of arms radially outward from the conduit to the expanded position, wherein the electrocautery wire is positioned directly adjacent an exterior of the wall of the organ when the plurality of arms is in the expanded position. In some embodiments, the plurality of arms are biased between the collapsed and expanded positions using a control wire coupled between the plurality of arms and the conduit.

At block 507, the method 500 may include retracting the tissue resection device towards the lumen of the organ to resection a targeted section of the wall. In some embodiments, block 507 includes energizing the electrocautery wire after the electrocautery wire is brought into position directly adjacent the exterior of the wall of the organ, and contacting the exterior of the wall of the organ with the electrocautery wire to penetrate the wall of the organ.

At block 509, the method 500 may optionally include securing a fastener, such as a clip, around an opening in the wall of the organ, the opening formed by removal of the targeted section of the wall. In some embodiments, block 509 includes first retracting the tissue resection device into an endoscopic tissue clamping device. In some embodiments, block 509 may include using a set of tissue latching barbs to engage the wall of the organ. For example, the surrounding tissue of the wall of the organ may be hooked onto the plurality of arms while resection of the targeted section of tissue is performed. The plurality of arms may then be collapsed and brought together, with the tissue latching barbs continuing to retain the tissue of the colon. The opening formed by the resection is thus shrunk and made easier for securement by the fastener.

In sum, embodiments herein describe approaches for using minimally invasive techniques to resect tissue, provide hemostasis, and close the defect left behind during FTR procedures. Approaches herein perform FTR by accessing the outside of the colon wall from the lumen, and then advancing the device back in towards the lumen until the targeted section of tissue is removed. Cutting is advantageously performed by means of electrocautery, which allows for hemostasis during the procedure and minimizes opportunity for post-operative leakage. Furthermore, embodiments herein advantageously include an electrocauterizing tip used to gain access to the outside of the colon wall, with precision and minimal potential for damage to adjacent anatomy. Focal FTR may be achieved as well as circumferential FTR using multiple segmented passes.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:
1. A tissue resection device, comprising:
  a conduit;
  a plurality of arms rotatably coupled to the conduit, each of the plurality of arms having a proximal end and a distal end opposite the proximal end, and being movable between a collapsed position and an expanded position, wherein the plurality of arms extends radially outward from the conduit in the expanded position;
  an electrocautery wire coupled to the plurality of arms, the electrocautery wire positionable directly adjacent an exterior tissue wall and proximal to the plurality of arms when the plurality of arms is in the expanded position; and
  a tissue latching barb extending from the distal end of each of the plurality of arms, wherein the tissue latching barb extends substantially perpendicularly from the distal end of each of the plurality of arms when the plurality of arms is in the expanded position wherein the proximal end of each of the plurality of arms is directly coupled to the conduit; and the distal end of each of the plurality of arms includes an opening receiving the electrocautery wire.
2. The tissue resection device of claim 1, further comprising an electrocautery tip extending from the plurality of arms, the electrocautery tip operable to perforate an interior tissue.

3. The tissue resection device of claim 2, wherein the electrocautery tip is integrally coupled with one or more of the plurality of arms.

4. The tissue resection device of claim 1, further comprising a control wire coupled to the plurality of arms and to the conduit, wherein the control wire is operable to move the arms between the collapsed position and the expanded position.

5. The tissue resection device of claim 4, wherein the control wire extends through an opening in the conduit, and wherein the control wire is directly coupled to each of the plurality of arms.

6. The tissue resection device of claim 1, the plurality of arms comprising three arms arranged circumferentially apart from one another by approximately 120°.

7. The tissue resection device of claim 1, the plurality of arms comprising two arms arranged circumferentially apart from one another by approximately 180°.

8. The tissue resection device of claim 1, wherein the electrocautery wire is a single wire extending between each of the plurality of arms to form a substantially triangular outline.

9. The tissue resection device of claim 1, further comprising a cover extending between each of the plurality of arms, the cover operable to capture a targeted section of tissue.

10. An endoscopic full thickness resection device, comprising:
   a conduit;
   a plurality of arms rotatably coupled to the conduit, each of the plurality of arms movable between a collapsed position and an expanded position, wherein each of the plurality of arms extends radially outward from the conduit in the expanded position and the plurality of arms are spaced circumferentially apart from one another by approximately 120°; and
   an electrocautery wire extending between a distal end of each of the plurality of arms, the electrocautery wire positioned directly adjacent an exterior tissue wall and proximal to the plurality of arms when the plurality of arms is in the expanded position.

11. The endoscopic full thickness resection device of claim 10, further comprising an electrocautery tip extending from the plurality of arms, the electrocautery tip operable to perforate an interior tissue wall when the plurality of arms is in the collapsed position.

12. The endoscopic full thickness resection device of claim 10, further comprising a control wire coupled between the plurality of arms and the conduit, wherein the control wire is operable to move the arms between the collapsed position and the expanded position.

13. A method for tissue resection comprising:
   positioning a tissue resection device within a lumen of an organ, the tissue resection device comprising:
      a conduit;
      a plurality of arms rotatably coupled to the conduit, each of the plurality of arms movable between a collapsed position and an expanded position; and
      an electrocautery wire coupled to the plurality of arms;
   penetrating a wall of the organ with the tissue resection device;
   extending the plurality of arms radially outward from the conduit to the expanded position, wherein the electrocautery wire is positioned directly adjacent an exterior of the wall of the organ and proximal to the plurality of arms;
   retracting the tissue resection device towards the lumen of the organ to resect a targeted section of the wall of the organ; and
   engaging the wall of the organ with a set of tissue latching barbs.

14. The method according to claim 13, further comprising:
   energizing the electrocautery wire after the electrocautery wire is brought into position directly adjacent the exterior of the wall of the organ; and
   contacting the exterior of the wall of the organ with the electrocautery wire to penetrate the wall of the organ.

15. The method according to claim 13, further comprising:
   providing an electrocautery tip extending from the plurality of arms; and
   perforating, when the plurality of arms is in the collapsed position, an interior tissue wall of the organ using the electrocautery tip.

16. The method according to claim 13, further comprising biasing the plurality of arms between the collapsed and expanded positions using a control wire coupled between the plurality of arms and the conduit.

17. The method according to claim 13, further comprising:
   retracting the tissue resection device into an endoscopic tissue clamping device; and
   securing a fastener around an opening in the wall of the organ, the opening formed by removal of the targeted section of the wall.

* * * * *